United States Patent [19]

Michejda et al.

[11] Patent Number: 4,923,970

[45] Date of Patent: May 8, 1990

[54] SUBSTITUTED 1-(2-CHLOROETHYL)-3-ACYL-3-ALKYL-TRIAZENES

[75] Inventors: Christopher J. Michejda, Gaithersburg; Richard H. Smith, Jr., Taneytown, both of Md.

[73] Assignee: Bionetics Research, Inc., Kensington, Md.

[21] Appl. No.: 179,622

[22] Filed: Mar. 28, 1988

[51] Int. Cl.$^5$ ............... C07C 115/00; C07C 107/00; C07C 107/02; A61K 31/655
[52] U.S. Cl. .................. 534/550; 260/349; 514/151; 534/553; 534/555
[58] Field of Search ............ 534/550, 553, 555

[56] References Cited

U.S. PATENT DOCUMENTS 3,088,789  5/1963  Breig et al. .......... 534/550 X

OTHER PUBLICATIONS

Le Blanc et al., Canadian J. Chem., vol. 50, No. 16, pp. 2544 to 2551, (1972).
Corey et al., J. Amer. Chem. Soc., vol. 94, pp. 6190 to 6191, (1972).
Fieser et al., "Reagents for Organic Synthesis", vol. 1, p. 1247, (1967).
R. H. Smith et al., VI, J. Org. Chem., vol. 53, pp. 1467–1471, (1988).
R. H. Smith et al., IV, J. Org. Chem., vol. 51, pp. 3751–3757, (1986).
R. H. Smith et al., I, Snythesis, pp. 476–478, (1983).
R. H. Smith et al., III, J. American Chem. Soc., vol. 108, pp. 3726–3730, (1986).
R. H. Smith et al., II, J. American Chem. Soc., vol. 106, pp. 1056–1059, (1984).
R. H. Smith et al., V, Cancer Letters, vol. 35, pp. 129–132, (1987).
D. E. V. Wilman, Cancer Treatment Reviews, vol. 15, pp. 69–72, (1988).
N. W. Gibson et al., Carcinogenesis, vol. 7, pp. 259–265, (1986).
D. J. Kohlsmith et al., Can. J. Physcio Pharm., vol. 62, pp. 396–402, (1984).

(List continued on next page.)

*Primary Examiner*—Floyd D. Nigel
*Attorney, Agent, or Firm*—John W. Schneller; William M. Blackstone

[57] ABSTRACT

A substituted 1-(2-chloroethyl)-3-acyl-3-alkyltriazene of the formula:

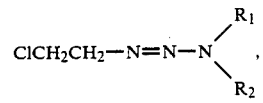

in which $R_1$ is 1-oxoalkyl containing from two to eight carbon atoms, fluorinated 1-oxoalkyls containing from two to eight carbon atoms and substituted with up to three fluorine atoms, benzoyl, phenylacetyl, carboalkoxy containing from two to eight carbon atoms, fluorinated carboalkyl containing from two to eight carbon atoms and up to three fluorine atoms, carbophenoxy, N-phenyl aminocarbonyl, N-alkyl aminocarbonyl containing from two to eight carbon atoms, thiocarbamoyl, N-alkylthiocarbamoyls with from two to eight carbon atoms, N-phenylthiocarbamoyl, dialkylphosphonates in which the alkyl groups can be the same or different and each contains from one to seven carbon atoms, phenylsulfonyl, and meta or para-substituted phenylsulfonyl in which the meta or para substituent is methyl, ethyl, methoxy, ethoxy, fluoro and chloro; and $R_2$ is indepedently alkyl containing from one to seven carbon atoms, fluoroalkyl containing from two to seven carbon atoms and from one to three fluorine atoms in which the $\alpha$ carbon of the fluoroalkyl group is not substituted with fluorine, benzyl, meta or para-substituted benzyl in which the meta or para substituent is chloro, fluoro, and alkoxy with from one to three carbon atoms, alkenyl containing from two to seven carbon atoms, and alkynyl containing from two to seven carbon atoms, useful as antitumor agents.

23 Claims, 1 Drawing Sheet

OTHER PUBLICATIONS

J. W. Lown et al., I, J. Org. Chem., vol. 47, pp. 851–856, (1982).

G. Eisenbrand, N-Nitroso Compounds: Occurrence, Biological Effects and Relevance to Human Cancer, pp. 695–708, (1985).

Y. F. Shealy et al., J. Pharm. Sci., vol. 64, pp. 177–180, (1975).

J. W. Lown et al., II, Can. J. Chem., vol. 59, pp. 1347–1356, (1981).

J. A. Montgomery, Cancer Treatment Reports, vol. 60, pp. 651–664, (1976).

J. E. N. Morten et al., Carcinogenesis, vol. 9, pp. 45–49, (1988).

D. B. Yarosh, Mutation Research, vol. 145, pp. 1–16, (1985).

O. Fodstad et al., Cancer Research, vol. 145, pp. 1778–1786, (1985).

M. F. G. Stevens et al., J. Med. Chem., vol. 27, pp. 196–201, (1984).

E. Sariban et al., Cancer Research, vol. 44, pp. 1352–1357, (1984).

Scheme 1
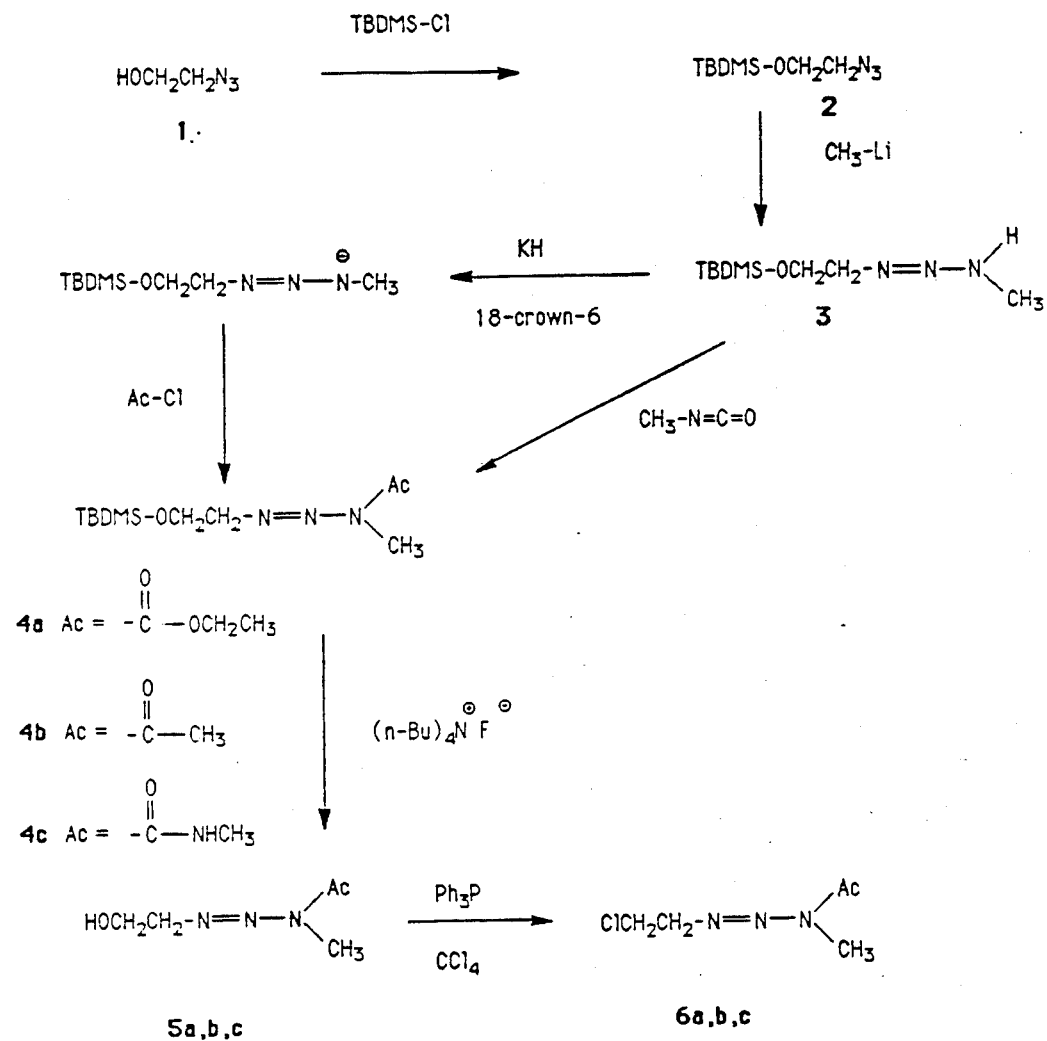

SUBSTITUTED 1-(2-CHLOROETHYL)-3-ACYL-3-ALKYLTRIAZENES

FIELD OF THE INVENTION

The present invention relates to novel 1-(2-chloroethyl)-3-acyl-3-alkyltriazenes and a method of synthesizing them.

TECHNOLOGY REVIEW

Substituted triazenes are potentially useful in the treatment of tumors because they are capable of alkylating DNA. For example, 1-aryl-3,3-dialkyltriazenes are known. One of these, 5-(dimethyltriazeno)imidazole-4-carboxamide (DTIC) is used clinically in the treatment of metastatic melanoma and some soft tissue sarcomas.

1,3-Dimethyl-3-acyltriazenes are also known. They may be synthesized by reacting methylazide with methyllithium, treating the resultant 1,3-dimethyltriazene (DMT) with potassium hydride to convert the DMT to an anion and reacting this anion with an acyl halide (Smith et al., *J. Org. Chem* 1986, 51, 3751).

Compounds such as dimethyltriazene and trimethyltriazene are too reactive for drug use. Substitution of an acyl group for a methyl at the 3- position to produce a 1,3-dimethyl-3-acyltriazene decreases the tendency of the triazene to hydrolyze, while retaining the ability to methylate DNA.

One disadvantage of using purely methylating agents to treat tumors is that while such agents may be effective they may also be carcinogenic themselves and so may cause additional tumors.

SUMMARY OF THE INVENTION

The present invention provides a series of 1-(2-chloroethyl)-3-acyl-3-alkyltriazenes of the formula

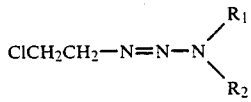

wherein $R_1$ is an acyl group as defined below, and $R_2$ is a carbon chain radical or substituted carbon chain radical as discussed below. The invention also provides a method of synthesis for these triazenes.

It is an object of the present invention to provide a new class of 3-acyltriazenes. It is also an object of the present invention to provide a new class of 3-acyltriazenes which are useful as antitumor agents. It is also an object of the present invention to provide a new class of 3-acyltriazenes which have decreased caroinogenicity compared to dimethylacyltriazenes. It is a further object of the present invention to provide a new class of chloroethylating agents which can be used in a variety of chemical environments, including in vivo environments as well as in vitro environments as a source of the chloroethyl group.

One advantage of the compounds of the present invention over the 1,3-dimethyl-3-acyltriazenes mentioned above is the substitution of a chlorethyl group for a methyl group at the 1- position. The reactive moiety derived from the compounds of the present invention is the 2-chloroethyl diazonium ion, a DNA cross-linking agent, which has been implicated as the cytotoxic agent from BCNU (N,N-bis(2-chloroethyl)-N-nitrosourea) and similar drugs.

The substitution of chloroethyl for methyl at the 1-position results in a molecule which is more stable than corresponding 1,3-dimethyl-3-acyltriazenes and thus provides an additional advantage.

The compounds of the present invention are also more stable in solution than known chloroethylaryltriazenes, and therefore more suitable for clinical use. Chloroethylaryltriazenes generally have a half-life on the order of minutes in solution at physiological pH and temperature, while the compounds of the present invention under the same conditions have half-lives on the order of hours or days.

It is expected that in vivo, enzymatic deacylation of the 1-(2-chloroethyl)-3-methyl-3-acyltriazene occurs, leading to the formation of 1-(2-chloroethyl)-3-methyltriazene. This compound is expected to act both as a methylating agent and a chloroethylating cross-linking agent for DNA. The compounds of the present invention therefore exhibit another advantage in that the repair enzyme $O^6$-alkylguanine-DNA alkyltransferase prefers to react with methyl groups on the $O^6$ position of guanine. Since the enzyme is destroyed during that reaction, this allows the 2-chloroethyl-modified DNA to undergo cytoxic cross-linking more efficiently than is the case for BCNU and similar drugs. The chloroethylacyltriazenes of the present invention are therefore expected to be stronqly cytotoxic. The compounds of the present invention are also expected to be less toxic to bone marrow (less myleosuppressive) than BCNU.

Additionally, BCNU on hydrolysis produces significant amounts of acetaldehyde in an alternate reaction path which decreases the amount of chloroethyl diazonium ion available for DNA crosslinking. This has also been observed for chloroethylaryltriazenes. In contrast, compounds of the present invention produce little or no acetaldehyde on hydrolysis and therefore have another advantage over the above-mentioned compounds.

Compounds of the present invention are also useful in chemical synthesis as chloroethylating agents, since solvolysis (for example, in water) at neutral pH leads to production of the chloroethyl diazonium ion.

BRIEF DESCRIPTION OF THE DRAWING

Scheme 1 shows the general method of synthesis. 2-Azidoethanol, (1), is treated with tert-butylchlorodimethylsilane to produce 1-azido-2-(tert-butyldimethylsiloxy)ethane (2). This is then treated with methyllithium (or other organometallic) to produce the corresponding 3-alkylated triazene (3). This compound is then acylated (4) either by treatment with an isocyanate or by treatment with KH in presence of a phase transfer catalyst to form an anion followed by reaction with an acyl halide, acid anhydride or similar acylating agents. The hydroxy group is then deprotected by treatment with tetra-n-butylammonium fluoride to produce the 2-hydroxyethyl triazene (5), and the chloride is then produced by reaction with $Ph_3P/CCl_4$ (6).

DESCRIPTION OF THE PREFERRED EMBODIMENTS

The acyl groups as defined in this application include: carbonyl with an alkyl substituent (1-oxoalkyl) containing from one to seven carbon atoms; or benzoyl; or phenylacetyl; carboalkoxy groups containing from two to eight carbon atoms, and fluorinated derivatives of these each containing up to three fluorine atoms; carbophenoxy; N-phenyl and N-methyl substituted aminocarbonyls; thiocarbamoyl; N-substituted thiocarbamoyls in which the substituent is an alkyl group with up to seven carbon atoms, or a phenyl group; dialkylphosphonates in which the alkyl groups can be the same or different and each contains from one to seven carbon atoms; and phenylsulfonyl or meta or para-substituted phenylsulfonyl, in which the meta or para substituent is a methyl or ethyl group, a methoxy or ethoxy group, or a halogen.

As can be seen from the above, a wide variety of acyl groups can be attached to the triazene skeleton to control the stability or decomposition of the triazene under specific conditions such as occur in vivo. Another method of controlling the reactivity of the triazenes of the invention is by varying the alkyl group at the 3-position. An electron-withdrawing substituent such as 3, 3, 3- trifluoropropyl, benzyl or the like, favors a decomposition pathway resulting in production of the chloroethyl diazonium ion (rather than an alkyl-diazonium ion) and therefore a higher degree of DNA cross-linking.

The substituent groups at the 3-position encompassed by this invention include: alkyl containing from one to seven carbon atoms, or such alkyl groups substituted with from one to three fluorine atoms wherein the $\alpha$ carbon of the alkyl group is not substituted with fluorine; benzyl or meta or para-substituted benzyl in which the meta or para substituent is chlorine or fluorine, or an alkoxy group with from one to four carbon atoms; and alkenyl or alkynyl groups containing from two to seven carbon atoms.

The following example will illustrate a method for synthesizing these compounds.

EXAMPLE

Safety Note. Triazenes are potent biological alkylating agents and as such should be considered to be toxic and potentially carcinogenic compounds. Efficient hoods and protective clothing should be used at all times in working with these substances. Alkyl azides are potentially explosively unstable and suitable precautions ought to be observed in the handling of these substances.

Materials. All chemicals were reagent grade (Aldrich), used as purchased without further purification. IR and UV spectra were obtained on a Perkin-Elmer Model 297 infrared spectrophotometer and a Hewlett-Packard Model 8450A double beam diode array processor, respectively. NMR spectra were obtained on a Varian XL-200 spectrometer. Exact mass measurements were determined on either a VG-Micromass, ZAB-2F (for FAB Spectra) or a VG 70-250 (for EI spectra) mass spectrometer. Mass measurements were confirmed by peak matching.

2-Azidoethanol, 1. 2-Chloroethanol (241.5 g, 3.0 mol) was added rapidly to a solution of sodium azide (234.5 g, 3.61 mol) in 800 mL of water at room temperature. The reaction mixture was stirred at 30° C. for 1 h and then at 70° C. for 24 h. The resulting red solution was cooled to room temperature, saturated with sodium sulfate, and extracted with 4x400 mL of methylene chloride. The combined organic layers were dried two times over anhydrous sodium sulfate and concentrated on a rotary evaporator at 25° C. to give 206 g (2.37 mol, 79.0%) of crude 2-azidoethanol. Although this substance can be purified by reduced pressure distillation (77° C., 24 mm), it was found that the above obtained material was of adequate purity to be used directly in the next reaction. This was also desirable given the highly explosive nature of low molecular weight organic azides.

1-Azido-2-(tert-butyldimethylsiloxy)ethane. 2. 2-Azidoethanol, 1, (105 g, 1.21 mol), crude from above preparation, and tert-butylchlorodimethylsilane (200 g. 1.33 mol) were dissolved in 200 mL of dry N,N-dimethylformamide (DMF) and stirred under nitrogen. Over a period of 20 min, imidazole (204 g, 3.00 mol) was added portionwise with stirring and the temperature of the reaction rose to about 40° C. The solution was stirred at 40° C. under nitrogen for 24 h. The reaction mixture was cooled to room temperature, poured into 1 L of water, and extracted with pentane (4×300 mL). The pentane layers were dried over anhydrous sodium sulfate, concentrated on a rotary evaporator at 25° C., and distilled at reduced pressure through a 4 in. Vigreux column to give 230 g (1.14 mol, 94.7%) of 1-azido-2-(tert-butyldimethylsiloxy)ethane, 2: bp 37°–39° C. (0.02 mm); IR (CH$_2$Cl$_2$) 2940, 2860, 2120, 1115, 940, 840 cm$^{10-1}$,$^1$H NMR (CDl$_3$, Me$_4$Si) $\delta$ 0.09 6H,s), 0.92 (9H,s), 3.27 (2H,t,J=5 Hz), 3.80 (2H,t,J=5 Hz); proton decoupled $^{13}$C NMR (CDCl$_3$, Me$_4$Si)) $\delta$-5.54, 18.18, 25.77, 53.16, 62.59.

1-(2-(tert-Butyldimethylsiloxy)ethyl)-3-methyltriazene, 3. A 1.4M ether solution of methyllithium (468 mL. 0.656 mol) was added dropwise over a period of 1.5 h to a stirred solution of 1-azido-2-(tertbutyldimethylsiloxy)ethane, 2, in anhydrous ether (200 mL) at −20° C. under nitrogen. [On occasion, the reaction mixture turned to a gel during the addition, necessitating the addition of sufficient anhydrous ether and mechanical agitation to disrupt the gel before completing addition of the methyllithium solution]. The resulting yellow solution was allowed to warm gradually to room temperature over 2 h. It was then cooled to 0° C. and hydrolyzed by careful addition of 100 mL of a 10% ammonium hydroxide solution containing 10% (w/v) ammonium chloride. The ether layer was separated and the aqueous layer was reextracted with pentane (300 mL). The ether and pentane layers were combined, dried over anhydrous sodium sulfate, and concentrated on a rotary evaporator at 25° C. Distillation at reduced pressure through a 4 in Vigreux column was then replaced with a short path distillation head and the distillation continued, yielding 54.2 g (0.419 mol, 70.4%) of 1-(2-(tert-butyldimethylsiloxy)ethyl)-3-methyltriazene, 3: bp 54°–56° C. (0.02 mm); IR (CH$_2$Cl$_2$) 3480, 2940, 2860, 1100, 840 cm$^{-1}$l; 1H NMR (CDCl$_3$, Me$_4$Si) $\delta$ 0.08 (6H,s), 0.89 (9H,s), 1.58 (1H,b), 3.23 (3H,b), 3.59 (2H,broad t,J=5 Hz), 3.83 (2H,t,J=5 Hz ; proton decoupled $^{13}$C NMR (CDCl$_3$, Me$_4$Si) $\delta$-5.36, 18.30, 25.86, (30.89) 46.73, 47.91 (60.98), (61.95) 62.80.

1-(2-(tert-Butyldimethylsiloxy]ethyl)-3-carboethoxy-3-methyltriazene, 4a. A solution of 1-(2-(tert-butyldimethylsiloxy)ethyl)-3-methyltriazene, 3, (24.0 g, 0.11 mol) in anhydrous ether (70 mL) was added dropwise over 1.5 h to a stirred suspension of potassium hydride ( - 6 g, 0.15 mol) in anhydrous ether containing 50 mg (1.3×10$^{-4}$ mol) of dicyclohexano-18-crown-6 ether at 25° C. under nitrogen. Stirring was continued for 30 min until hydrogen evolution had ceased. The reaction mixture was cooled to −30° C. and then ethyl chloroformate (13.1 g, 0.12 mol) in anhydrous ether (70 mL) was added dropwise with stirring over 2 h. the reaction was stirred and allowed to warm gradually to 0° C. over 30 minutes, at which time hydrolysis was accomplished by the careful addition of 250 mL of 10% ammonium hydroxide solution containing 10% (w/v) ammonium chloride. The ether layer was separated and the aqueous layer was reextracted with pentane (100 mL). The ether and pentane layers were combined and dried twice over anhydrous sodium sulfate, and concentrated on a rotary evaporator at 25° C. Distillation of 1/10 of the crude product at reduced pressure using a short path distillation head gave 1.68 g ($6.45 \times 10^{-2}$ mol, 58.6% yield based on the fraction of total product distilled) of 1-(2-(tert-butyldimethylsiloxy)ethyl)-3-carboethoxy-3-methyltriazene, 4a: bp 90°–95° C. (0.07 mm); IR(Cl$_4$) 2960, 2940, 2860, 1725, 1160, 840 cm$^{-1}$; $^1$H NMR (CDCl$_3$, Me$_4$Si) δ 0.04 (6H,s), 0,87 (9H,s), 1.37 (3H,t,J=7 Hz), 3.24 (3H,s), 3.92 (2H,m), 4.94 (2H,m), 4.38 (2H,q,J=7 Hz); proton decoupled $^{13}$C NMR (CDCl$_3$, Me$_4$Si) δ-5.36, 14.45, 18.21, 25.89, 29.41, 61.20, 62.87, 63.87, 154.5. The crude product was determined to be sufficiently pure to be used directly in the following reaction.

3-Carboethoxy-2-(2-hydroxyethyl)-3-methyltriazene. 5a. A 1.0M tetrahydrofuran solution of tetra-n-butylammonium fluoride (140 mL, 0.14 mol) was added portionwise over 5 min with stirring to a solution of 1-(2-(tert-butyldimethylsiloxy)ethyl)-3-carboethoxy-3-methyltriazene, 4a, (29.0 g, 0.133 mol) in tetrahydrofuran (20 mL). The reaction solution was heated to 35° C. and stirring continued for 30 min. The volume of the reaction was reduced by one half on a rotary evaporator at 25° C. and the resultant solution was chromatographed on a column of 300 g of Silica Gel 60 (EM, neutral, 70–230 mesh) packed in 1:1 pentane-ether. The column was eluted with 4 L of ether with about 20 psi head pressure of nitrogen. The first 200 mL of eluent contained a large amount of an oil assumed to be tert-butylfluorodimethylsilane. Remaining eluent fractions contained a mixture of three or four components with one substance (rf 0.35 on F-60 silica gel plate, EM, eluted with ether and visualized by short wavelength UV light). These fractions were recombined (18.6 g) and rechromatographed on a column of 200 g of Silica Gel 60 packed in pentane and eluted sequentially with 500 mL each of pentane; 25%, 50%, and 75% ether in pentane, and finally with 2 L of ether. The first liter of ether eluent contained the desired product, 3-carboethoxy-1-(2-hydroxyethyl)-3-methyltriazene, 5a, 4.58 g (0.026 mol, 19.5%). Attempts to further purify this substance by reduced pressure (0.002 mm) distillation generally failed as a result of thermal decomposition during distillation. IR (CH$_2$Cl$_2$) 3600, 3460, 2940, 1710, 1155, 990 cm$^{-1}$; UV (CH$_3$CN) $\lambda_{max}$233 (log ε 4.14); $^1$H NMR (CDCl$_3$, Me$_4$Si) δ1.36 (3H,t,7 Hz), 1.66 ($^1$H,b), 3.25 (3H,s), 3.98 (4H,s), 4.37 (2H,g,J=7 Hz); proton decoupled $^{13}$C NMR (CDCl$_3$, Me$_4$Si) δ 14.48*, 29.53, 61.02, 63,14, 63.38* 154.4* (*=attached proton test, APT, indicated odd number of protons attached); exact mass calcd m/z for C$_6$H$_{14}$N$_3$O$_3$ (M+1 by FAB) 176.1035, found 176.1031.

3-Carboethoxy 1-(2 chloroethyl)-3-methyltriazene. 6a. A solution of triphenylphosphine (2.83 g, $1.08 \times 10^{-2}$ mol) and 3-carboethoxy-1-(2-hydroxyethyl)-3-methyltriazene, 5a. (1.89 g, $1.08 \times 10^{-2}$ mol) in 25 mL of carbon tetrachloride (dried over 3A molecular sieves) was refluxed overnight under nitrogen. The reaction mixture was cooled to room temperature and diluted with pentane (100 mL). After standing at 10° C. for four hours, the reaction mixture was filtered through a pad of Celite to remove precipitated triphenylphosphine oxide. The filtrate was concentrated on a rotary evaporator at 22° C., redissolved in a minimum amount of ether and chromatographed on a column of 40 g of Silica Gel 60 packed in 1:10 ether-pentane and eluted with 200 mL each of 10%, 20% and 30% ether in pentane. The first 200 mL of eluent contained 1.4 g of a yellow oil. Distillation of that oil at reduced pressure with a short path distillation apparatus produced 1.22 g ($6:30 \times 10^{-3}$ mol, 58.3%) of the desired compound, 3-carboethoxy-(2-chloroethyl)-3-methyltriazene, 6a:bp 60°–62° C. (0.003 mm); IR (CCl$_4$) 2990, 2970, 1730, 1155, 990 cm$^{10-1}$; UV (CH$_3$CN) λ max 2333 (log ε 4.19); $^1$H NMR 9CDCl$_3$, Me$_4$Si) δ 1.39 (0-CH$_2$CH$_3$,t,J=7 Hz), 3.28 (NCH$_3$,s), 3.88 (Cl-CH$_2$,t,J=6 Hz), 4.12 (CH$_2$CH-N.t,J=6Hz), 4.39 (0—CH$_2$CH$_3$,q,J=7 Hz); proton decoupled $^{13}$C NMR (CDCl$_3$, Me$_4$Si) δ 14.47 (0—CH$_2$CH$_3$), 29.76 (N—CH$_3$), 41.92 (Cl—CH$_2$), 62.50 (CH$_2$—N), 63.17 (0—CH$_2$CH$_3$), 154.27 (C50 0); ($^1$H and $^{13}$C NMR assignments made via $^{13}$C -APT and 2D-heteronuclear correlated spectrum (2D-COSY) experiments); exact mass calcd m/z for C$_6$H$_{12}$N$_3$O$_2$Cl 193.0618, found 193.0629 (by EI).

3-Acetyl-1-(2-(tert-butyldimethylsiloxy)ethyl)-3-methyltriazene, 4b. A solution of 1-(2-(tert-butyldimethylsiloxy)ethyl)-3-methyltriazene, 3, (21.74 g. 0.10 mol) in ether (50 mL) was added dropwise over 1.5 h to a stirred suspension of potassium hydride (4.41 g, 0.11 mol) in anhydrous ether containing 50 mg ($1.3 \times 10^{-4}$ mol) of dicyclohexano-18-crown-6 ether at room temperature under nitrogen. When hydrogen evolution had ceased, the reaction mixture was cooled to $-10°$ C. and a solution of acetyl chloride (8.64 g, 0.11 mol) in ether (40 mL) was added dropwise over 2 h. The reaction mixture was allowed to warm to 0° C. over 1 h and hydrolyzed by the addition of 75 mL of 10% ammonium hydroxide containing 10% (w/v) of ammonium chloride. The ether layer was separated and the aqueous layer was extracted with pentane (2×100 mL). The organic layers were combined, dried over anhydrous sodium sulfate, and concentrated on a rotary evaporator. The residue was distilled at reduced pressure through a 4 in. Vigreux distillation column to give, after a small forefraction, 15.7 g (0.0645 mol, 64.5%) of 3-acetyl-1-(2-(tert0butyldimethylsiloxy)-ethyl)-3-methyltriazene, 4b: bp 78°–84° C. (0.08 mm); IR (CH$_2$Cl$_2$) 2960, 2950, 2860, 1685, 1150, 1105, 980, 840 cm$^{10-1}$; $^1$H NMR $_3$DCl$_2$, Me$_4$Si) δ 0.04 (6H,s), 0.86 (9H,s), 2.43 (3H,s), 3.21 (3H,s), 3.93 (2H,t.J=5 Hz), 4.00 (2H,t,J=5 Hz); proton decoupled $^{13}$C NMR CDCl$_3$, Me$_4$Si) δ-5.32, 18.20, 21.83, 25.75, 26.60, 61.00, 64.50, 173.2.

3-Acetyl-I-(2-hydroxyethyl)-3-methyltriazene, 5b. A 1.0M solution (68 mL) of tetra-n-butylammonium fluoride in tetrahydrofuran was added dropwise to a stirred solution of 3-acetyl-1-(2-(tert-butyldimethyl-siloxy)ethyl)-3-methyltriazene, 4b, in tetrahydrofuran at 0 ° C. The reaction solution was allowed to warm gradually to room temperature over 1 h. The volume of the solution was reduced 50% with a rotary evaporator at 25° C. and the residue was chromatographed on a column of 200 g of Silica Gel 60 (EM, neutral, 70–230 mesh) packed in 3:1 ether-pentane. The column Was eluted with 4 L of 4:1 ether-pentane. The last 3 L of solvent were concentrated on a rotary evaporator to give 6.75 g (0.0465 mol, 72.5%) of 3-acetyl-1-(2-hydroxethyl)-3-methyltriazene, 5b, as a colorless oil, which fails to distill satisfactorily at reduced pressure (0.002 mm). IR (CH$_2$Cl$_2$) 3600, 3470, 2940, 1680, 1140, 975 cm$^{10-1}$; UV (CH$_3$CN) $\lambda_{max}$ 237 (log ε4.09); $^1$H NMR (CDCl$_3$, Me$_4$Si) δ 2.09 (1H,b), 2.44 (3H,s), 3.22 (3H,s), 3.96

(2H,m), 4.04 (2H,m); proton decoupled $^{13}$C NMR (CDCl$_3$, Me$_4$Si)δ 21.83 (CH$_3$), 26.80 (CH$_3$), 60.85 (CH$_2$), 64.00 (CH$_2$), 173.15 (C=O) [APT experiment allowed assignment of the number of attached protons]; exact mass calcd. m/z for C$_5$H$_{11}$N$_3$O$_2$ 145.0851, found 145.0848 (by EI).

3-Acetyl-1-(2-chloroethyl)-3-methyltriazene, 6b. A solution of triphenylphosphine (5.89 g, 2.25×10$^{-2}$ mol) and 3-carboethoxy-1-(2 hydroxyethyl)-3-methyltriazene, 5b, (2.9 g, 2.0×10$^{-2}$ mol) in 50 mL of carbon tetrachloride (dried over 3A molecular sieves) was refluxed overnight under nitrogen. The reaction mixture was cooled to room temperature and diluted with pentane (250 mL). After standing at 10° C. overnight, the reaction mixture was filtered through a pad of Celite to remove precipitated triphenylphosphine oxide. The filtrate was concentrated on a rotary evaporator at 220° C., the residue (4.2 g) was dissolved in a minimum amount of ether and chromatographed on a column of 35 g of Silica Gel 60 packed in 10% ether in pentane and eluted with 600 mL of this same solvent mixture. Evaporation of the eluent on a rotary evaporator and vacuum transfer (40° C./0.005 mm) of the residue gave 1.94 g 0.0119 mol, 59.6%) of 3-acetyl-1-(2-chloroethyl)-3-methyltriazene, 6b; IR (CCl$_4$) 2970, 1710, 1515, 1145, 990 cm$^{10-1}$; UV (CH$_3$CN) λ$_{max}$ 238 (log ϵ 4.23); $^1$H NMR (CDCl$_3$, Me$_4$Si) δ 3.45 (CH$_3$,s), 3.23 (N—CH$_3$,s), 3.90 (Cl—CH$_2$,t,J=5.5 Hz), 4.12 (CH$_2$-N,t,J=5.5 Hz); proton decoupled $^{13}$C NMR (CDCl$_3$, Me$_4$Si) δ 21.85 (CH$_3$(, 26.92 (N—C H$_3$), 41.78 Cl—CH$_2$), 62.68 (CH$_2$—N), 63.17 (O—CH$_2$CH$_3$), 173.0 (C=O); exact mass calcd. m/z for C$_5$H$_{10}$N$_3$OCl 163.0512, found 163.0506 (by EI).

1-(2-(tert-Butyldimethylsiloxy)ethyl)-3-(N-methylcarbamoyl)-triazene, 4c. Methyl isocyanate (5.99 g. 0.105 mol) was added dropwise to a stirred solution of 1-(2-(tert-butyldimethylsiloxy)ethyl)-3-methyltriazene, 3, (21.74 g, 0.10 mol) in pentane (75 mL), under nitrogen, and at such a rate to maintain a gentle reflux. Following this addition, the reaction mixture was stirred at 30° C. for 30 min and then concentrated on a rotary evaporator at 25° C. to yield 27.17 g of 1-(2-(tert-butyl-dimethylsiloxy)ethyl)-3-methyl-3-(N-methylcarbamoyl)triazene as a colorless oil. $^1$H NMR (CDCl$_3$, Me$_4$Si) δ 0.01 6H, s), 0.84 (9H,s), 2.92 (3H,d,J=5Hz), 3.22 (3H,s), 3.82 (2H,t,J=5Hz), 3.97 2H,t,J-5Hz , 6.35 (1H,b); proton decoupled $^{13}$C NMR (CDCl$_3$, Me$_4$Si.) δ -5.35, 18.25, 25.79, 26.86, 27,53, 61.12, 155.64.

1-(2-Hydroxyethyl)-3-methyl-3-(N-methylcarbamoyl)triazene. 5c. A 1.0M solution (100 mL) of tetra-n-butylammonium fluoride in tetrahydrofuran was added dropwise to a stirred solution of 1-(2-(tert-butyldimethylsiloxy)ethyl)-3-methyl-3-(N-methylcarbamoyl)triazene in tetra-hydrofuran at −10° C. over 1 h. The volume of the solution was then reduced 50% with a rotary evaporator at 25° C. and the resultant solution was chromatographed on a column of 250 g of Silica Gel 60 (EM, neutral, 70–230 mesh) packed in ether. The column was eluted with 5 L of ether. The last 3 L of eluent were concentrated on a rotary evaporator and the residue (6.7 g) recrystallized from methylene chloride-ether to give 4.24 g of 1-(2-hydroxyethyl)-3-methyl-3-(N-methylcarbamoyl)triazene, 5c, (0.0265 mol, 27.8%): mp 72°–74° C.; IR (CH$_2$Cl$_2$) 3600, 3450, 2955, 1690, 1510, 1190, 1050 cm$^{10-1}$; UV (CH$_3$CN) λ $_{max}$245 (log ϵ 4.04); $^1$H NMR (CDCl$_3$, Me$_4$Si) δ 1.78 ($^1$H ,t,J=6 Hz), 2.94 (3H,d,J=5 Hz), 3.26 (3H,s), 3.97 (2H,t,J=5 Hz), 4.02 (2H,m-A$_2$B$_2$X), 6.34 (1H,b); proton decoupled $^{13}$C NMR (CDCl$_3$, Me$_4$Si) δ 26.86, 27.60, 60.72, 155.54; exact mass calcd m/z for C$_5$H$_{12}$N$_4$O$_2$160.0960, found 160.0967 (by EI).

1-(2-Chloroethyl)-3-methyl-3-(N-methylcarbamoyl)-triazene, 6c. A solution of triphenylphosphine (6.22 g, 2.37×10$^{-2}$ mol) and 3-carboethoxy-1-(2-hydroxyethyl)3-methyltriazene, 5 c. (3.8 g, 2.37×10$^{-2}$ mol) in 60 mL of carbon tetrachloride (dried over 3A molecular sieves) was refluxed overnight under nitrogen. The reaction mixture was cooled to room temperature and diluted with pentane (220 mL). After standing at 10° C. overnight, the reaction mixture was filtered through a pad of Celite to remove precipitated tiiphenylphosphine oxide. The filtrate was concentrated on a rotary evaporator at 22° C., redissolved in a minimum amount of ether and chromatographed on a column of 35 g of Silica Gel 60 packed in 10% ether in pentane and eluted with 350 mL each of 10, 20, 30, 40 and 50% ether in pentane. Concentration of the last 1L of eluent on a rotary evaporator and recrystallization of the residue from ether-pentane gave 2.38 g of 1-(2-chloroethyl)-3-methyul-3-(N-methylcarbamoyl)triazene, 6c, (0.0133 mol, 56.2%):mp 48.5°–49.5° C.; IR (CCl$_4$) 3460, 3400 (weak), 2970, 2910, 1705, 1500, 1190, 1070, 1050 cm$^{10-1}$; UV (CH$_3$CN) λ$_{max}$ 245.5 (log ϵ 4.05); $^1$H NMR (CDCl$_3$ (CDCl$_3$, Me$_4$Si) δ 2.95 (NH-CH$_3$,d,J=5 Hz), 3.26 (N-CH$_3$, s), 3.86 (CH$_2$-Cl,t,J=6 Hz , 4.05 CH$_2$-N,t,J=6 Hz), 6.37 (N-H,b); proton decoupled $^{13}$C NMR ((CDCl$_3$, Me$_4$Si) δ 26.87 (NH-CH$_3$), 27.70 (N-CH$_3$), 41.97 (CH$_2$-Cl), 62.43 (CH$_2$-N), 155.2 (C=O); ($^1$H and $^{13}$H NMR assignments made via $^{13}$C-ApT and 2D-COSY spectra); exact mass calcd m/z for C$_5$H$_{11}$N$_4$OCl 178.0621, found 178.0598 (by EI).

It will be understood that the above description of the present invention is susceptible to various modifications, changes and adaptations, and the same are intended to be comprehended within the meaning and range of equivalents of the appended claims.

What is claimed is:

1. A substituted 1-(2-chlorethyl)-3-acyl-3-alkyltriazene of the formula:

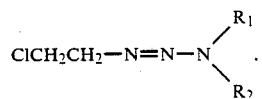

wherein R$_1$ is selected from the group consisting of
   1-oxoalkyl containing from two to eight carbon atoms, fluorinated 1-oxoalkyls containing from two to eight carbon atoms and substituted with up to three fluorine atoms, benzoyl, phenylacetyl, carboalkoxy containing from two to eight carbon atoms, fluorinated carboalkoxy containing from two to eight carbon atoms and up to three fluorine atoms, carbophenoxy, N-phenyl aminocarbonyl, N-alkyl aminocarbonyl containing from two to eight carbon atoms, thiocarbamoyl, N-alkylthiocarbamoyls with from two to eight carbon atoms, N-phenylthiocarbamoyl, dialkylphosphonates in which the alkyl groups can be the same or different and each contains from one to seven carbon atoms, phenylsulfonyl, and meta or para-substituted phenylsulfonyl in which the meta or para substituent is selected from the group consisting of methyl, ethyl, methoxy, ethoxy, fluoro and chloro;

and wherein $R_2$ is independently selected from the group consisting of alkyl containing from one to seven carbon atoms, fluoroalkyl containing from two to seven carbon atoms and from one to three fluorine atoms in which the α carbon of the fluoroalkyl group is not substituted with fluorine, benzyl, meta or para-substituted benzyl in which the meta or para substituent is selected from the group consisting of chloro, fluoro, and alkoxy with from one to three carbon atoms, alkenyl containing from two to seven carbon atoms, and alkynyl containing from two to seven carbon atoms.

2. A 1-(2-chloroethyl)-3-acyl-3-alkyltriazene as defined in claim 1, wherein $R_1$ is a 1-oxoalkyl group containing from two to eight carbon atoms.

3. A 1-(2-chloroethyl)-3-acyl-3-alkyltriazene as defined in claim 1, wherein $R_1$ is a fluorinated 1-oxoalkyl group containing from two to eight carbon atoms and substituted with up to three fluorine atoms.

4. A 1-(2-chloroethyl)-3-acyl-3-alkyltriazene as defined in claim 1, wherein $R_1$ is benzoyl.

5. A 1-(2-chloroethyl)-3-acyl-3-alkyltriazene as defined in claim 1, wherein $R_1$ is phenylacetyl.

6. A 1-(2-chloroethyl)-3-acyl-3-alkyltriazene as defined in claim 1, wherein $R_1$ is a carboalkoxy group containing from two to eight carbon atoms.

7. A 1-(2-chloroethyl)-3-acyl-3-alkyltriazene as defined in claim 1, wherein $R_1$ is a fluorinated carboalkoxy group containing from two to eight carbon atoms and up to three fluorine atoms.

8. A 1-(2-chloroethyl)-3-acyl-3-alkyltriazene as defined in claim 1, wherein $R_1$ is carbophenoxy.

9. A 1-(2-chloroethyl)-3-acyl-3-alkyltriazene as defined in claim 1, wherein $R_1$ is N-phenyl aminocarbonyl.

10. A 1-(2-chloroethyl)-3-acyl-3-alkyltriazene as defined in claim 1, wherein $R_1$ is an N-alkyl aminocarbonyl containing from two to eight carbon atoms.

11. A 1-(2-chloroethyl)-3-acyl-3-alkyltriazene as defined in claim 1, wherein $R_1$ is thiocarbamyl.

12. A 1-(2-chloroethyl)-3-acyl-3-alkyltriazene as defined in claim 1, wherein $R_1$ is an N-alkylthiocarbamyl containing from two to eight carbon atoms.

13. A 1-(2-chloroethyl)-3-acyl-3-alkyltriazene as defined in claim 1, wherein $R_1$ is N-phenylthiocarbamyl.

14. A 1-(2-chloroethyl)-3-acyl-3-alkyltriazene as defined in claim 1, wherein $R_1$ is a dialkylphosphonate in which the alkyl groups can be the same or different and each contains from one to seven carbon atoms.

15. A 1-(2-chloroethyl)-3-acyl-3-alkyltriazene as defined in claim 1, wherein $R_1$ is phenylsulfonyl.

16. A 1-(2-chloroethyl)-3-acyl-3-alkyltriazene as defined in claim 1, wherein $R_1$ is meta or para-substituted phenylsulfonyl in which the meta or para substituent is selected from the group consisting of methyl, ethyl, methoxy, ethoxy, fluoro and chloro.

17. A 1-(2-chloroethyl)-3-acyl-3-alkyltriazene as defined in claim 1, wherein $R_2$ is an alkyl group containing from one to seven carbon atoms.

18. A 1-(2-chloroethyl)-3-acyl-3-alkyltriazene as defined in claim 1, wherein $R_2$ is a fluoroalkyl group containing from two to seven carbon atoms and from one to three fluorine atoms in which the α carbon of the fluoroalkyl group is not substituted with fluorine.

19. A 1-(2-chloroethyl)-3-acyl-3-alkyltriazene as defined in claim 1, wherein $R_2$ is benzyl.

20. A 1-(2-chloroethyl)-3-acyl-3-alkyltriazene as defined in claim 1, wherein $R_2$ is meta or para-substituted benzyl in which the meta or para substituent is selected from the group consisting of chloro, fluoro, and alkoxy with from one to three carbon atoms.

21. A 1-(2-chloroethyl)-3-acyl-3-alkyltriazene as defined in claim 1, wherein $R_2$ is alkenyl containing from two to seven carbon atoms.

22. A 1-(2-chloroethyl)-3-acyl-3-alkyltriazene as defined in claim 1, wherein $R_2$ is alkynyl containing from two to seven carbon atoms.

23. A process for synthesizing a 1-(2-chloroethyl)-3-acyl-3-alkyltriazene as defined in claim 1, comprising the steps of:

protecting the hydroxy group of 2-azidoethanol with tert-butylchloro-dimethylsilane to produce 1-azido-2-(tertbutyl-dimethylsiloxy)ethane;

reacting 1-azido-2-(tert-butyldimethylsiloxy)ethane with an alkyllithium, alkenyllithium or alkynyllithium to produce a corresponding 3-substituted triazene;

acylating the 3-substituted triazene with an isocyanate or by treatment with potassium hydride in presence of a phase transfer catalyst to form an anion followed by reaction with an acylating agents; and deprotecting the hydroxy group by treatment with tetra-n-butylammonium fluoride; and forming a chloride by reacting the hydroxy group with $Ph_3P/CCl_4$.

* * * * *

UNITED STATES PATENT AND TRADEMARK OFFICE
CERTIFICATE OF CORRECTION

PATENT NO. : 4,923,970
DATED : May 8, 1990
INVENTOR(S) : Christopher J. Michejda et al.

It is certified that error appears in the above-identified patent and that said Letters Patent is hereby corrected as shown below:

Column 1, line 5, please insert the following new paragraph:

--Pursuant to contract No. 1-CO-23909 awarded by the Department of Health and Human Services, the United States Government has rights in this invention.--

Signed and Sealed this

Second Day of November, 1993

Attest:

BRUCE LEHMAN

*Attesting Officer*  *Commissioner of Patents and Trademarks*